(12) United States Patent
Yamada et al.

(10) Patent No.: US 8,256,275 B2
(45) Date of Patent: Sep. 4, 2012

(54) IN-LIQUID-SUBSTANCE DETECTION SENSOR

(75) Inventors: Hajime Yamada, Ishikawa-gun (JP);
Naoko Aizawa, Yasu (JP); Yoshihiro Koshido, Yasu (JP); Koji Fujimoto, Otsu (JP); Toru Yabe, Konan (JP); Michio Kadota, Kyoto (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 391 days.

(21) Appl. No.: 12/555,894

(22) Filed: Sep. 9, 2009

(65) Prior Publication Data

US 2009/0320574 A1    Dec. 31, 2009

Related U.S. Application Data

(63) Continuation of application No. PCT/JP2008/053386, filed on Feb. 27, 2008.

(30) Foreign Application Priority Data

Mar. 29, 2007 (JP) ................................. 2007-089317

(51) Int. Cl.
*G01N 29/00* (2006.01)
(52) U.S. Cl. ............ 73/64.53; 73/24.01; 73/24.06; 73/31.06; 73/61.75; 310/313 R
(58) Field of Classification Search .......... 73/24, 24.06, 73/61.45, 61.49, 61.75, 61.79, 64.53; 257/415; 310/313 R
See application file for complete search history.

(56) References Cited

U.S. PATENT DOCUMENTS

| 6,543,274 | B1 | 4/2003 | Herrmann et al. |
| 7,353,710 | B2* | 4/2008 | Oikawa et al. .................. 73/703 |
| 7,389,673 | B2* | 6/2008 | Kimura et al. ............... 73/24.06 |
| 7,656,070 | B2* | 2/2010 | Kadota et al. ............. 310/313 R |
| 2004/0207033 | A1* | 10/2004 | Koshido ........................ 257/415 |

(Continued)

FOREIGN PATENT DOCUMENTS

EP          1 761 104 A1    3/2007

(Continued)

OTHER PUBLICATIONS

Official Communication issued in International Patent Application No. PCT/JP2008/053386, mailed on May 27, 2008.

*Primary Examiner* — Hezron E Williams
*Assistant Examiner* — Hoang Nguyen
(74) *Attorney, Agent, or Firm* — Keating & Bennett, LLP

(57) ABSTRACT

An in-liquid-substance detection sensor that achieves size reduction and detection accuracy improvement includes a piezoelectric substrate, at least two SAW devices provided on one major surface of the piezoelectric substrate and each having at least one IDT electrode defining a sensing portion, outer electrodes provided on the other major surface of the piezoelectric substrate and electrically connected to the SAW devices through vias extending through the piezoelectric substrate, a channel-defining member provided on the one major surface of the piezoelectric substrate so as to surround the SAW devices and a region connecting the SAW devices to each other, thereby defining sidewalls of a channel, and a protective member bonded to the one major surface of the piezoelectric substrate with the channel-defining member interposed therebetween, thereby sealing the channel, the protective member having at least two through holes communicating with the channel.

8 Claims, 9 Drawing Sheets

U.S. PATENT DOCUMENTS

| | | |
|---|---|---|
| 2006/0131731 A1 | 6/2006 | Sato |
| 2006/0192462 A1 | 8/2006 | Iwamoto et al. |
| 2009/0051245 A1* | 2/2009 | Takayama et al. ........ 310/313 R |
| 2009/0174285 A1* | 7/2009 | Kando ...................... 310/313 R |
| 2009/0236935 A1* | 9/2009 | Kando ...................... 310/313 R |

FOREIGN PATENT DOCUMENTS

| | | |
|---|---|---|
| JP | 08-181563 A | 7/1996 |
| JP | 11-201951 A | 7/1999 |
| JP | 2003-502616 A | 1/2003 |
| JP | 2004-129222 A | 4/2004 |
| JP | 2005-038946 A | 2/2005 |
| JP | 2006-162318 A | 6/2006 |
| JP | 2006-173557 A | 6/2006 |
| JP | 2006-184011 A | 7/2006 |
| JP | 2006-267184 A | 10/2006 |
| JP | 2007-520698 A | 7/2007 |
| WO | 2005/066621 A1 | 7/2005 |
| WO | 2005/120130 A1 | 12/2005 |
| WO | 2006/006343 A1 | 1/2006 |
| WO | 2006/008940 A1 | 1/2006 |
| WO | 2006/027945 A1 | 3/2006 |
| WO | 2006/114829 A1 | 11/2006 |

* cited by examiner

IN-LIQUID-SUBSTANCE DETECTION SENSOR

BACKGROUND OF THE INVENTION

1. Field of the Invention

The present invention relates to in-liquid-substance detection sensors, and in particular, to an in-liquid-substance detection sensor including a surface acoustic wave (SAW) device.

2. Description of the Related Art

Some in-liquid-substance detection sensors, which detect substances contained in liquids, include SAW devices.

For example, an in-liquid-substance detection sensor 131, shown in FIGS. 8 and 9 as a perspective view and an exploded perspective view, respectively, includes a base substrate 132 and protective members 134 and 136 bonded to both surfaces of the base substrate 132 with adhesion layers 133 and 135 interposed therebetween. SAW device chips 137 and 138 having sensing portions are mounted on the top surface of the base substrate 132 by flip-chip bonding. As shown in FIG. 10 as a cross-sectional view, this mounting is performed such that bump electrodes 116a and 116b are sealed by a resin layer 117. One SAW device chip 137 includes a reaction film 113 covering interdigital-transducer (IDT) electrodes (comb-shaped electrodes) 109 and 110, functioning as the sensing portions, provided on a piezoelectric substrate 108.

A liquid is supplied into a through hole 136a provided in the protective member 136, and flows through a through hole 135a into a first channel 133a, when the liquid touches the sensing portions of the SAW device chip 137. The liquid further flows through a through hole 135e into a second channel 133b, when the liquid touches the sensing portions of the SAW device chip 138. The liquid then flows from an end of the channel 133b into a through hole 135b, and is discharged from a through hole 136b provided in the protective member 136.

In the in-liquid-substance detection sensor configured as described above, since the SAW device chips are mounted on the top surface of the base substrate by flip-chip mounting, size reduction is limited. Moreover, if the resin layer that seals the bump electrodes, provided for mounting the SAW device chips, absorbs the liquid or is melted by being in contact with the liquid, and thus the bump electrodes come into contact with the liquid, the reliability of the in-liquid-substance detection sensor is reduced. Further, if accuracy in mounting the two SAW device chips is poor, it becomes difficult to provide the channels with high accuracy. In addition, the use of two SAW device chips deteriorates the detection accuracy if there is a significant difference between the characteristics of the devices.

SUMMARY OF THE INVENTION

In light of the above, preferred embodiments of the present invention provide an in-liquid-substance detection sensor whose size can be reduced easily and whose detection accuracy can be improved easily.

An in-liquid-substance detection sensor according to a preferred embodiment of the present invention includes a piezoelectric substrate, at least two SAW devices provided on one major surface of the piezoelectric substrate and each having at least one IDT electrode defining a sensing portion, outer electrodes provided on the other major surface of the piezoelectric substrate and electrically connected to the SAW devices through vias extending through the piezoelectric substrate, a channel-defining member provided on the one major surface of the piezoelectric substrate so as to surround the SAW devices and a region connecting the SAW devices to each other, thereby defining sidewalls of a channel, and a protective member bonded to the one major surface of the piezoelectric substrate with the channel-defining member interposed therebetween, thereby sealing the channel, the protective member having at least two through holes communicating with the channel.

In the foregoing configuration, a fluid, such as a liquid or a gas, is supplied through one of the through holes provided in the protective member. When the fluid flows through the channel, the fluid touches the sensing portions of the at least two SAW devices. The substance contained in the fluid causes changes at the sensing portions of the SAW devices. These changes are detected by utilizing electrical signals supplied through outer electrodes.

With the foregoing configuration in which the SAW devices are directly disposed on the surface of the channel, the size of the in-liquid-substance detection sensor can be reduced easily, compared with the case where SAW device chips are mounted on a base substrate. Since the need for mounting SAW device chips is eliminated, there is no possibility that the reliability of the in-liquid-substance detection sensor may be reduced because of melting of the resin layer that seals the bump electrodes provided for mounting the SAW device chips. Moreover, compared with the case where SAW device chips are mounted on a base substrate, the positional accuracy of the SAW devices relative to the channel is improved. Thus, it becomes easy to form the channel with high accuracy. In addition, by simultaneously forming a plurality of SAW devices on the piezoelectric substrate, the difference between the characteristics of the SAW devices can be reduced, whereby the detection accuracy can be improved easily.

The channel-defining member is preferably made of resin.

In this case, the piezoelectric substrate and the protective member can be bonded together, with the channel-defining member interposed therebetween, with a low manufacturing cost.

The channel-defining member is preferably made of photosensitive resin.

In this case, the sidewalls of the channel can be formed by, for example, a photolithographic technique with ease and high accuracy.

The protective member is preferably made of resin film.

In this case, the piezoelectric substrate and the protective member can be bonded together, with the channel-defining member interposed therebetween, with a low manufacturing cost.

The protective member is preferably made of photosensitive resin film.

In this case, the through holes of the protective member can be provided by, for example, a photolithographic technique with ease and high accuracy.

The protective member is preferably made of an inorganic material.

In this case, the rigidity of the protective member is increased, whereby the in-liquid-substance detection sensor can have a robust structure.

The difference between coefficients of linear expansion of the protective member and the piezoelectric substrate is preferably about 2 ppm/° C. or smaller, for example.

In this case, the in-liquid-substance detection sensor is resistant to heat stress and causes only a negligible warpage. Accordingly, it becomes easy to process a plurality of the in-liquid-substance detection sensors in units of wafers (groups of substrates).

The protective member and the piezoelectric substrate are preferably made of the same material.

In this case, the in-liquid-substance detection sensor becomes more resistant to heat stress and causes only a much smaller, minimal warpage. Accordingly, it becomes much easier to process a plurality of the in-liquid-substance detection sensors in units of wafers (groups of substrates).

According to preferred embodiments of the present invention, the size reduction and detection accuracy improvement of the in-liquid-substance detection sensor are easily realized.

Other features, elements, steps, characteristics and advantages of the present invention will become more apparent from the following detailed description of preferred embodiments of the present invention with reference to the attached drawings.

BRIEF DESCRIPTION OF THE PREFERRED EMBODIMENTS

Figure 3A:
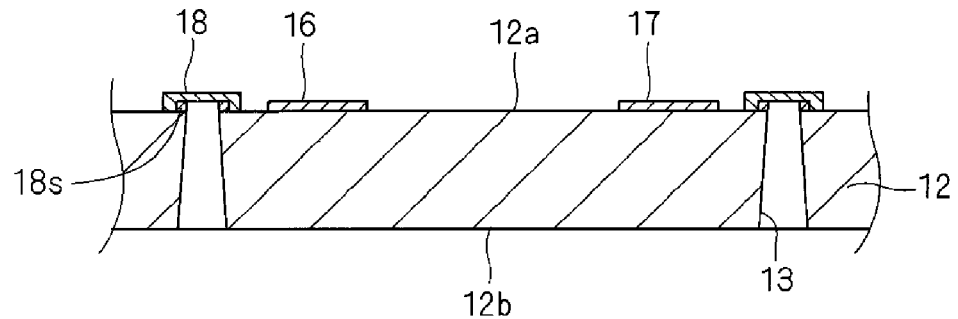
Figure 3B:
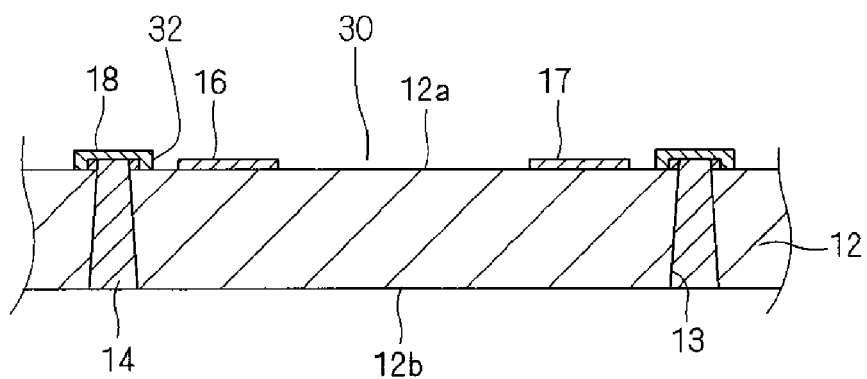
Figure 3B:
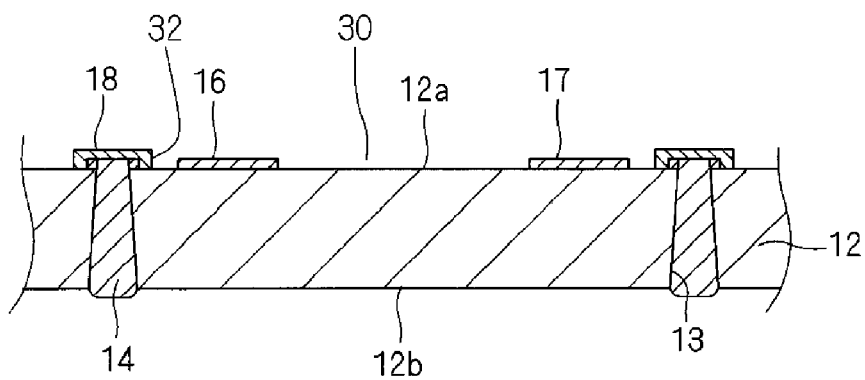
Figure 3C:
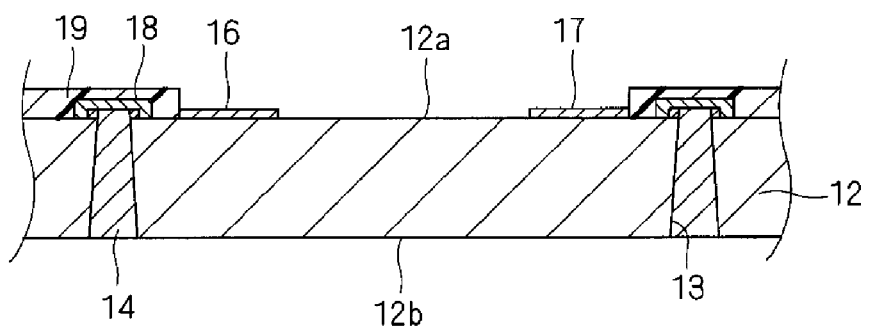

FIGS. 3A-3C include cross-sectional views illustrating a method of manufacturing the in-liquid-substance detection sensor according to the first preferred embodiment of the present invention.

FIGS. 4D-4G include cross-sectional views illustrating the method of manufacturing the in-liquid-substance detection sensor according to the first preferred embodiment of the present invention.

Figure 5:
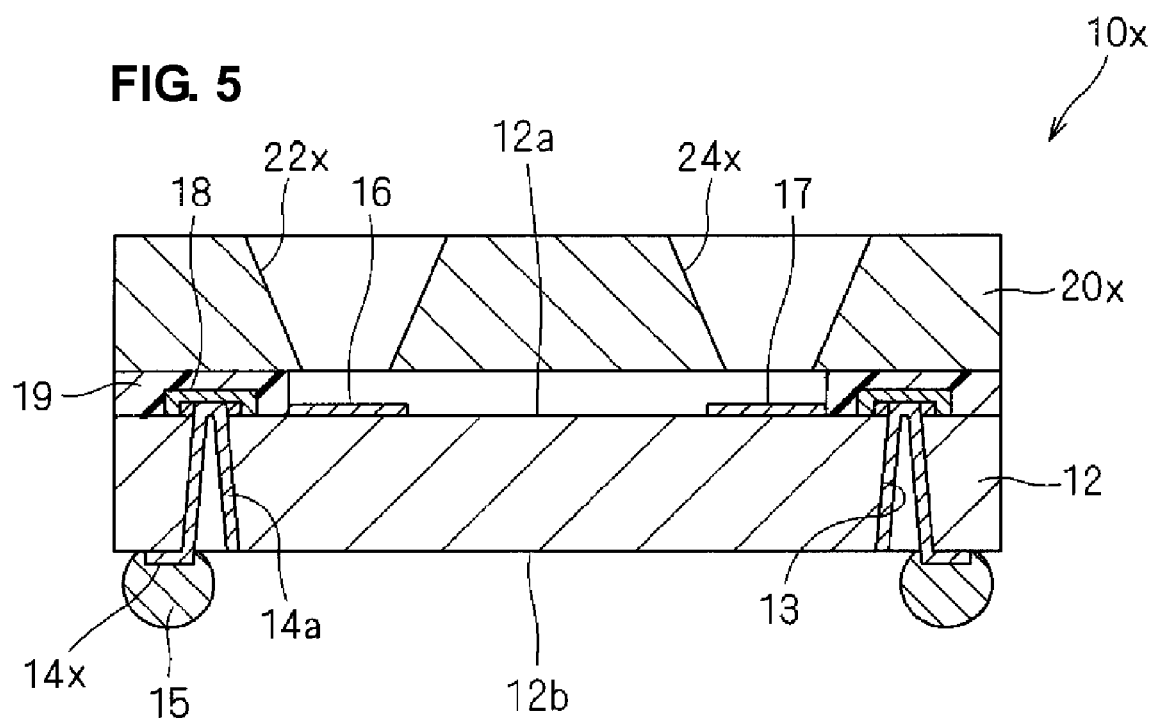

FIG. 5 is a cross-sectional view of another in-liquid-substance detection sensor according to a second preferred embodiment of the present invention.

Figure 6A:
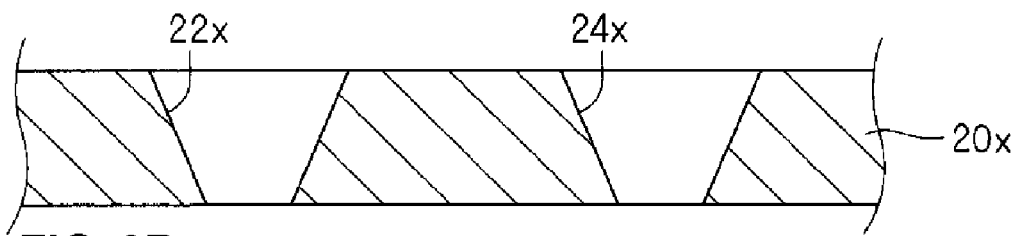
Figure 6B:
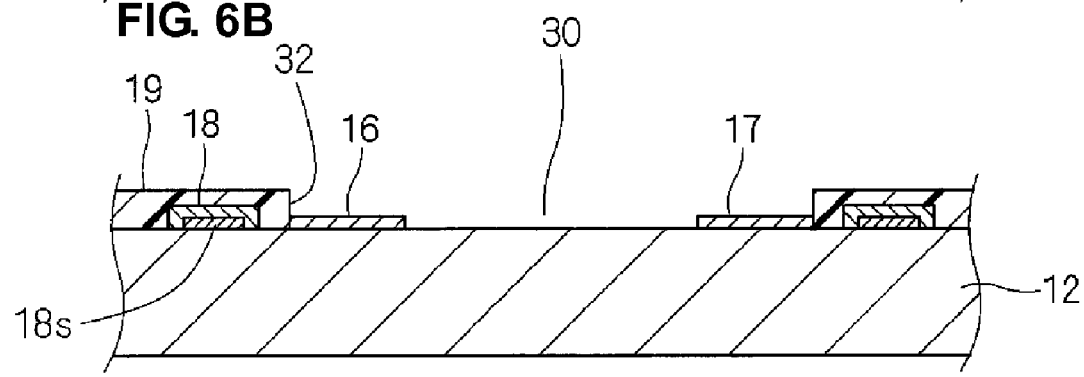
Figure 6C:
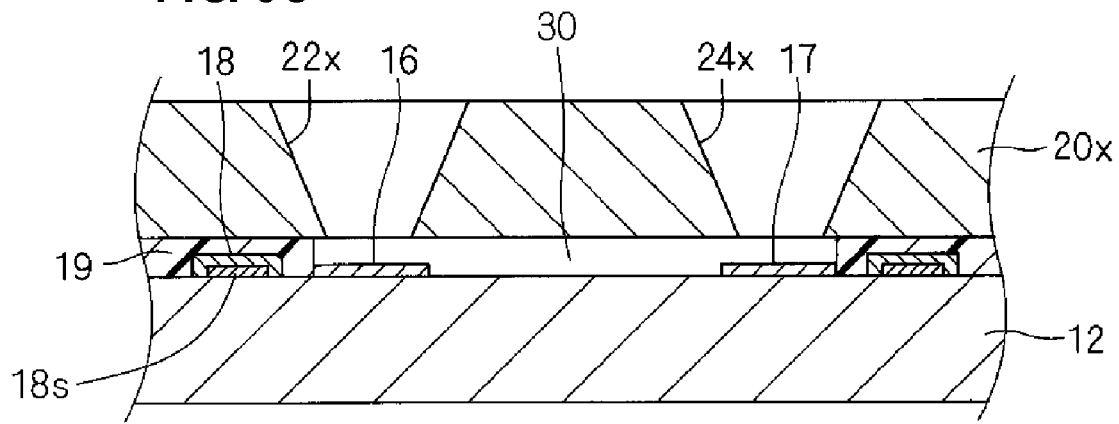

FIGS. 6A-6C include cross-sectional views illustrating a method of manufacturing the in-liquid-substance detection sensor according to the second preferred embodiment of the present invention.

FIGS. 7D-7G include cross-sectional views illustrating the method of manufacturing the in-liquid-substance detection sensor according to the second preferred embodiment of the present invention.

Figure 8:
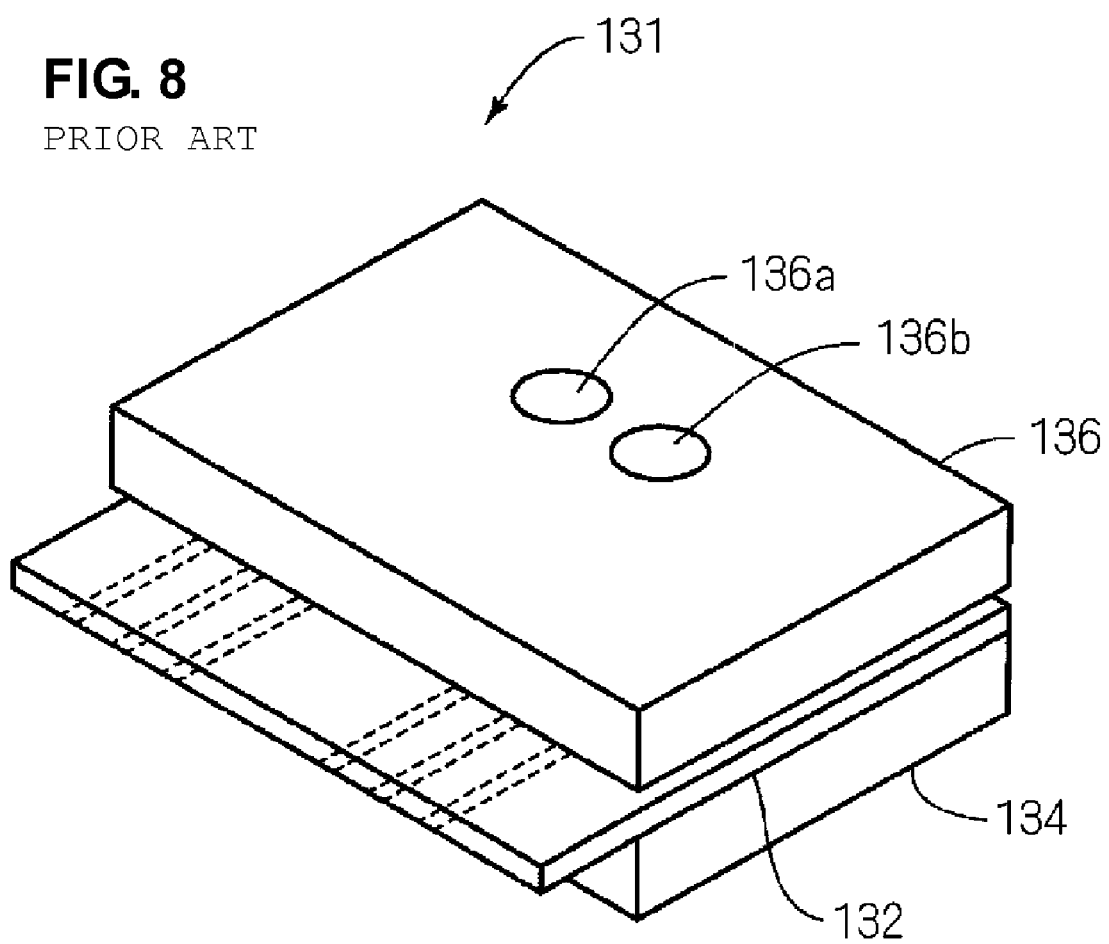

FIG. 8 is a perspective view of a conventional in-liquid-substance detection sensor.

Figure 9:
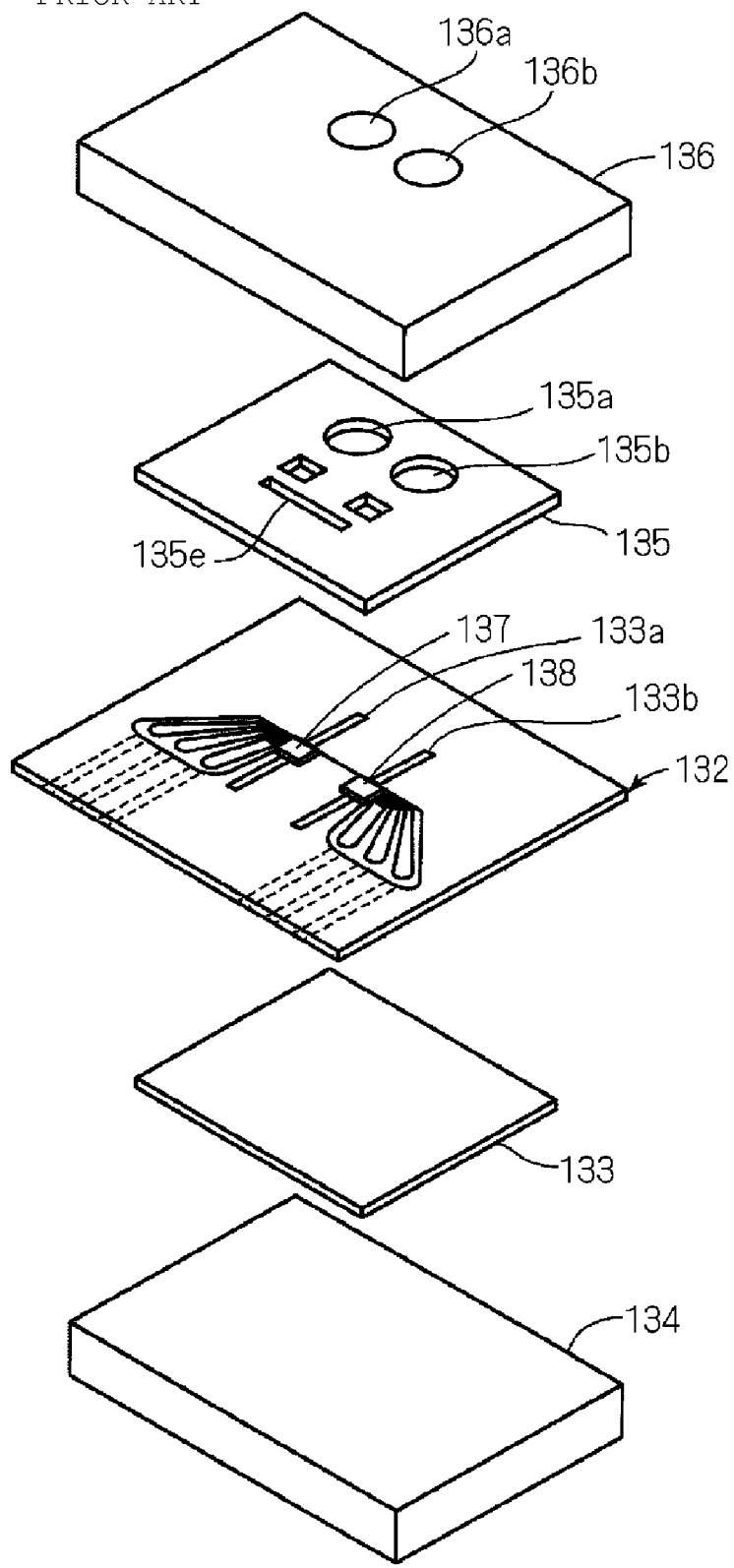

FIG. 9 is an exploded perspective view of the conventional in-liquid-substance detection sensor.

Figure 10:
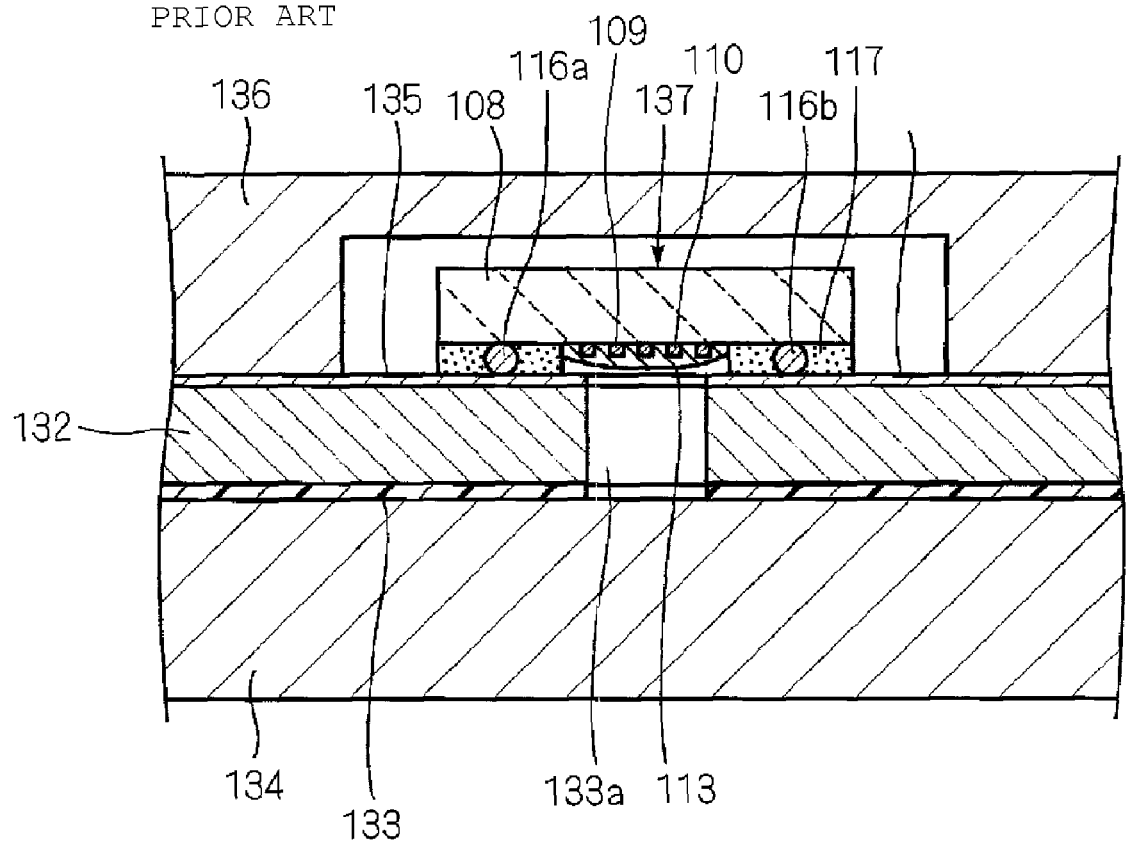

FIG. 10 is an enlarged cross-sectional view of relevant elements included in the conventional in-liquid-substance detection sensor.

DETAILED DESCRIPTION OF THE PREFERRED EMBODIMENTS

Preferred embodiments of the present invention will now be described with reference to FIGS. 1 to 7G.

First Preferred Embodiment

An in-liquid-substance detection sensor 10 according to a first preferred embodiment will be described with reference to FIGS. 1 to 4G.

Figure 1:
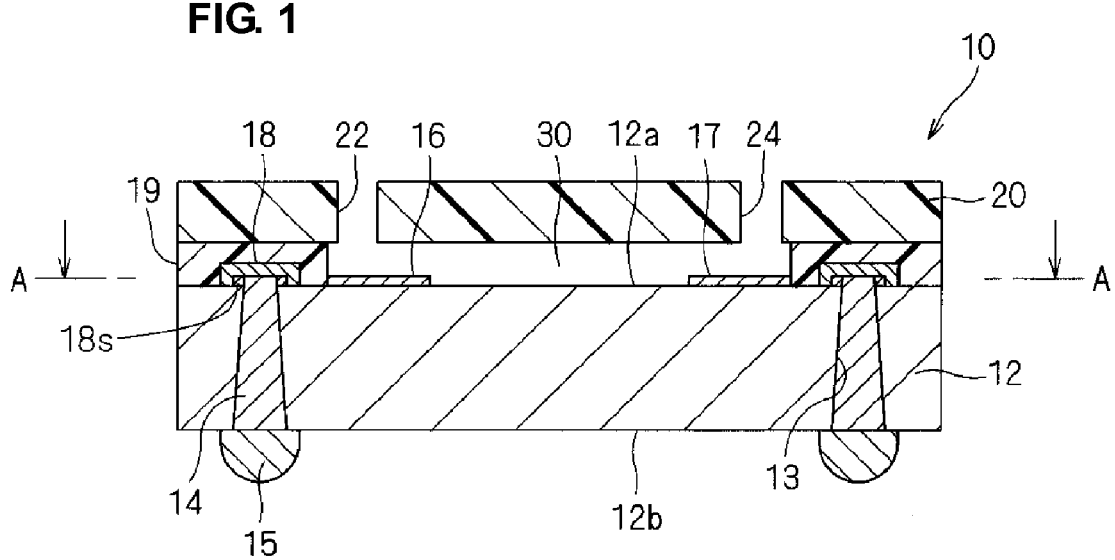
FIG. 1 is a cross-sectional view of an in-liquid-substance detection sensor according to a first preferred embodiment of the present invention.
Figure 2:
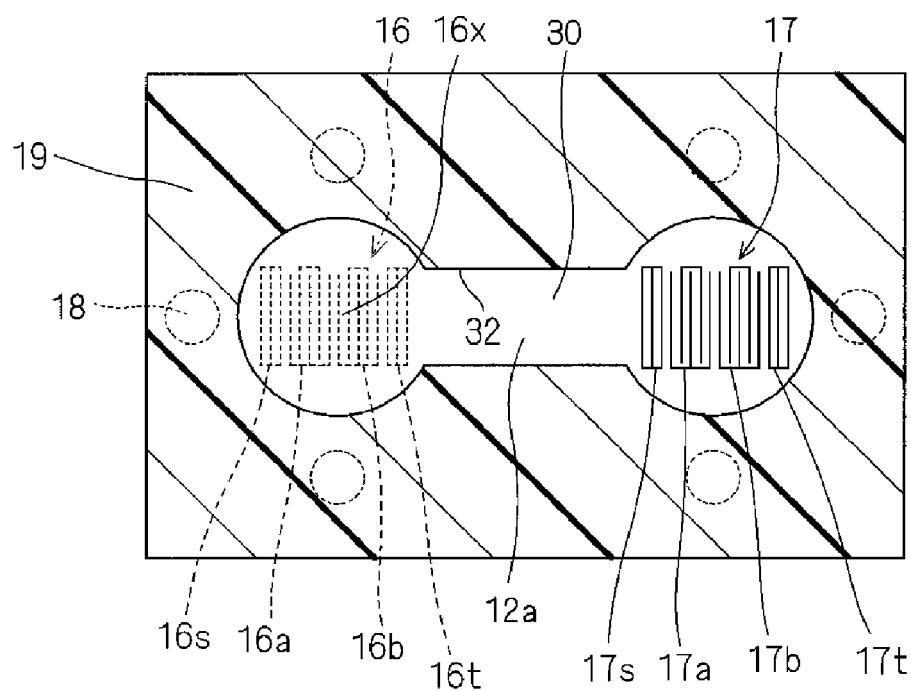
FIG. 2 is a sectional view taken along the line A-A in FIG. 1.

As shown in FIGS. 1 and 2 as a cross-sectional view and a sectional view taken along the line A-A in FIG. 1, respectively, the in-liquid-substance detection sensor 10 includes a piezoelectric substrate 12 and a lid member 20 bonded together with a support layer 19 interposed therebetween. The piezoelectric substrate 12 is provided on a back surface 12b thereof, remote from the lid member 20, with solder bumps 15 functioning as outer electrodes. For example, the piezoelectric substrate 12 is composed of $LiTaO_3$, the lid member 20 is made of resin film, and the support layer 19 is made of adhesive resin.

The piezoelectric substrate 12 is provided on a top surface 12a thereof, facing the lid member 20, with a conduction pattern of metal film formed by deposition or other suitable process. The conduction pattern includes two SAW devices 16 and 17, electrode pads 18, and connection patterns (not shown) connecting the SAW devices 16 and 17 to the electrode pads 18.

As schematically shown in FIG. 2, the SAW devices 16 and 17 include IDT electrodes 16a and 16b, and 17a and 17b arranged in a direction in which a vibration as a surface acoustic wave propagates, and reflectors 16s and 16t, and 17s and 17t arranged on both sides of the IDT electrodes 16a and 16b, and 17a and 17b.

The piezoelectric substrate 12 has through holes or vias 13. The through holes or via 13 are each filled with an in-via electrode 14. The in-via electrode 14 electrically connects a corresponding one of the electrode pads 18 on the top surface 12a of the piezoelectric substrate 12 to a corresponding one of the solder bumps 15 on the bottom surface 12b of the piezoelectric substrate 12.

The lid member 20 has through holes 22 and 24 at respective positions facing the two SAW devices 16 and 17. The through holes 22 and 24 of the lid member 20 may alternatively be provided at positions remote from the SAW devices 16 and 17, not directly thereabove, although the size of the entire configuration becomes a little large.

As shown in FIG. 2, the support layer 19 is arranged so as to surround the two SAW devices 16 and 17 and a region connecting the two SAW devices 16 and 17 to each other, thereby defining sidewalls 32 of a channel 30.

The in-liquid-substance detection sensor 10 is supplied with a fluid, such as a liquid or a gas, through one through hole 22 of the lid member 20. The supplied fluid flows through the channel 30 from one SAW device 16 to the other SAW device 17 toward the other through hole 24 of the lid member 20.

As shown in FIG. 2, the one SAW device 16 is covered with a reaction film 16x. Specifically, the reaction film 16x covers the entirety of the IDT electrodes 16a and 16b and the reflectors 16s and 16t. The reaction film 16x contains a material that is bondable to a detection-target substance contained in the fluid. When the fluid touches the reaction film 16x and the detection-target substance in the fluid bonds to the reaction film 16x, the vibration propagation characteristic of the surface acoustic wave changes in accordance with, for example, a change in the characteristic of the reaction film 16x. This changes an electrical signal that is output from the SAW device 16. By utilizing such a phenomenon, the detection-target substance in the fluid can be detected. In the drawings other than FIG. 2, the reflection film is not shown.

The vibration propagation characteristic of the other SAW device 17, having no reaction film thereon, is not affected by the presence/absence of the detection-target substance in the fluid. Therefore, by comparing the electrical signal outputs from the SAW devices 16 and 17, accuracy in detecting the detection-target substance in the fluid can be improved.

An exemplary method of manufacturing the in-liquid-substance detection sensor 10 will now be described with reference to FIGS. 3A-3C and FIGS. 4D-4G showing cross-sectional views.

A wafer (parent substrate) having a plurality of the in-liquid-substance detection sensors 10 is prepared, and the wafer is divided into child substrates.

First, as shown in FIG. 3A, the vias 13 are provided in the piezoelectric substrate 12, having the SAW devices 16 and 17, by a method such as sandblasting, laser application, wet etching, ion milling, or the like. Considering the processing rate, sandblasting is most suitable for via-processing.

If sandblasting is performed, electrodes, functioning as etch-stop layers 18s, composed of Cu or the like are provided below the respective electrode pads 18, with a thickness that is about 2% or more larger, for example, than the thickness of the piezoelectric substrate 12. For example, for an approximately 350 μm-thick $LiTaO_3$ substrate, the etch-stop layers 18s are formed with a thickness of about 10 μm.

Subsequently, as shown in FIG. 3B, the in-via electrodes 14 are formed by electroplating, conductive-paste application, or the like. Electrical signals are acquired through the in-via electrodes 14 from the top surface 12a to the bottom surface 12b of the piezoelectric substrate 12. Considering the coating and filling characteristics of the electrodes with respect to the inner walls of the vias, electroplating, in particular Cu electroplating, is suitable for formation of the in-via electrodes 14. As shown in FIG. 3B', outer electrodes may alternatively be obtained by making the in-via electrodes 14 project from the bottom surface 12b by about 10 μm.

Subsequently, as shown in FIG. 3C, the support layer 19 is formed by applying adhesive resin on the top surface 12a of the piezoelectric substrate 12. For example, an epoxy-based or polyimide-based photosensitive resin is applied and is photolithographically patterned. The thickness of the support layer 19 is set to be sufficient for allowing the sample to flow, specifically, for example, about 100 μm or larger in a case where the sample is blood or the like.

Figure 4D:
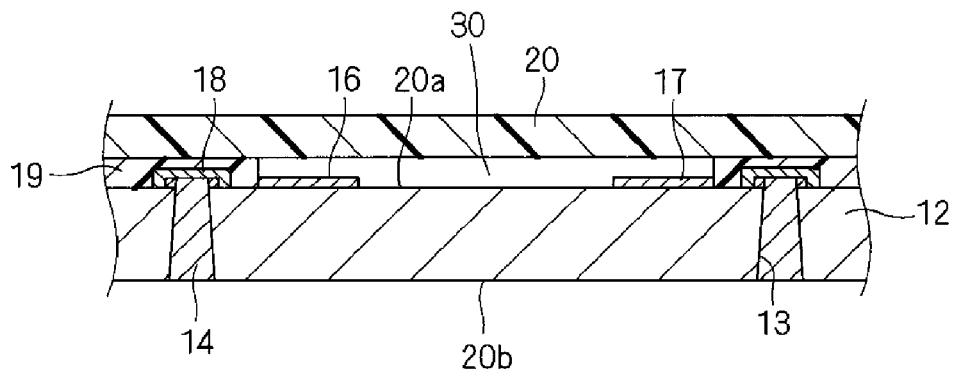
Figure 4E:
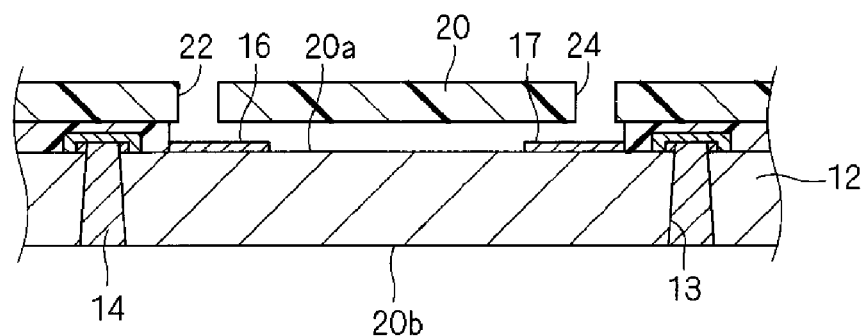

Subsequently, as shown in FIG. 4D, an epoxy-based or polyimide-based resin film is provided so as to form the lid member 20. The resin film is laminated onto the support layer 19, and, as shown in FIG. 4E, the through holes 22 and 24 for introduction and discharge of the sample are provided therein. For example, the through holes 22 and 24 are processed by using a third-harmonic-generation (THG) laser. In a case where the lid member 20 is made of photosensitive resin film, the through holes 22 and 24 can be processed photolithographically. Therefore, smears and heat damage to devices that often occur in laser processing can be reduced.

Figure 4F:
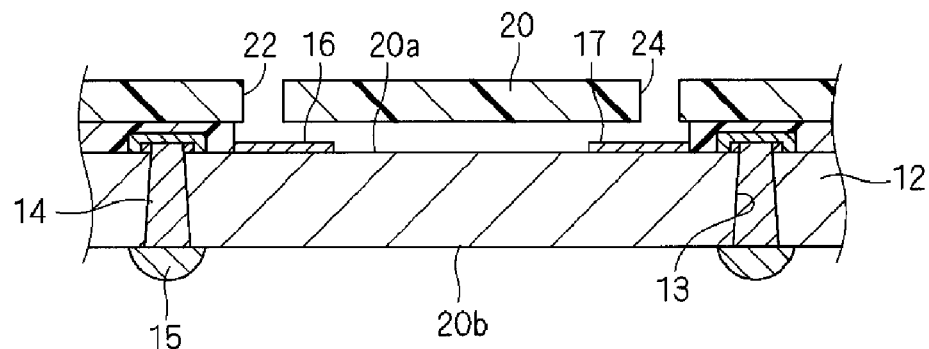

Subsequently, as shown in FIG. 4F, the solder bumps 15 are formed by solder paste printing and reflowing. In the case where the vias 13 are filled with electroplating, conductive paste, or the like, the solder bumps 15 can be provided directly on the vias. In a case where the vias 13 are not filled, the solder bumps 15 are provided beside the respective vias 13, as described below in a second preferred embodiment.

Figure 4G:
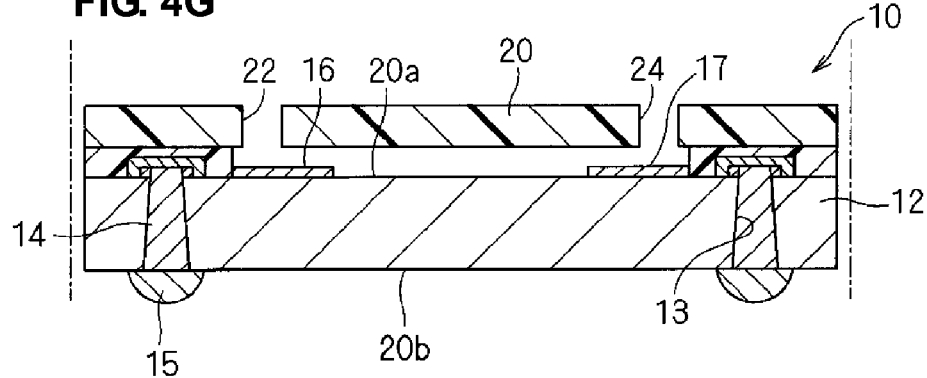

Subsequently, as shown in FIG. 4G, the parent substrate is divided into chips (child substrates) each having the in-liquid-substance detection sensor 10 by dicing, laser application, or the like.

Alternatively, the in-liquid-substance detection sensor 10 may be manufactured in a process flow other than that described above.

As described above, the channels and vias of the in-liquid-substance detection sensors 10 are formed in units of wafers, and are therefore easily processed. This also leads to reductions in size, height, and manufacturing cost of the in-liquid-substance detection sensor 10.

The lid member 20 is preferably made of resin film. Therefore, the channel can be formed in a simple manner with a low manufacturing cost.

The SAW devices 16 and 17 are provided at the bottom of the channel 30. Therefore, compared with the case where SAW device chips are mounted on a base substrate, the sample can be efficiently made to flow through sensing portions of the SAW devices. Accordingly, only a small amount of sample is necessary, and accurate sensing is possible.

In addition, since no terminals are provided on a surface to be in contact with the sample, such as liquid, characteristics of the in-liquid-substance detection sensor are not deteriorated, and the reliability of the in-liquid-substance detection sensor is improved. Moreover, the need to cover terminals with a resin layer or the like is eliminated, leading to an easy manufacturing process.

The two SAW devices can be formed simultaneously on a single substrate by a single method. Therefore, there is substantially no difference between the characteristics of the devices, and good detection accuracy can be obtained.

The in-liquid-substance detection sensor has a flat top surface. Therefore, a device for supplying a liquid, for example, can be easily set onto the sensor.

The channels are formed in units of wafers. Therefore, the channels can be formed with high accuracy. Accordingly, the detection accuracy is improved.

The signals are acquired from the bottom surface through the vias to the outer electrodes (solder bumps or Cu, Au, or Ni bumps). Therefore, a parasitic inductor does not change. This stabilizes device characteristics, leading to stable device formation.

Second Preferred Embodiment

An in-liquid-substance detection sensor according to the second preferred embodiment will now be described with reference to FIGS. 5 to 7G.

An in-liquid-substance detection sensor 10x of the second preferred embodiment has substantially the same configuration as the in-liquid-substance detection sensor of the first preferred embodiment. Hereinafter, differences between the two will be mainly described, and like reference numerals will denote like elements.

As shown in FIG. 5 as a cross-sectional view, the in-liquid-substance detection sensor 10x includes, substantially the same as in the first preferred embodiment, a piezoelectric substrate 12 and a lid member 20x bonded together, with a support layer 19 interposed therebetween. The piezoelectric substrate 12 has two SAW devices 16 and 17 on a top surface 12a thereof.

Unlike in the first preferred embodiment, the lid member 20x is a piezoelectric substrate composed of, for example, $LiTaO_3$. The lid member 20x has through holes 22x and 24x, substantially the same as in the first preferred embodiment.

The piezoelectric substrate 12 has vias or through holes 13, as in the first preferred embodiment. Unlike in the first preferred embodiment, however, in-via electrodes 14a spread over the inner walls of the respective vias 13, and extend beyond the vias 13 to a bottom surface 12b of the piezoelectric substrate 12. Solder bumps 15, which are to function as outer electrodes, are provided on extensions 14x of the in-via electrodes 14a, i.e., beside the vias 13. If electrical signals can be acquired from the outside with sufficient electrical conduction, the bumps 15 may be omitted and the in-via electrodes 14x may be made to function as outer terminals.

An exemplary method of manufacturing the in-liquid-substance detection sensor 10x will now be described with reference to FIGS. 6A-6C and FIGS. 7D-7G showing cross-sectional views.

As shown in FIG. 6A, the vias (through holes) 22x and 24x for introduction and discharge of the sample are provided in the lid member 20x. The vias are provided by sandblasting, laser application, wet etching, ion milling, or other suitable process.

Subsequently, as shown in FIG. 6B, the support layer 19 is formed by providing adhesive resin on the top surface 12a of the piezoelectric substrate 12 having the SAW devices 16 and 17 thereon. For example, an epoxy-based or polyimide-based photosensitive resin is applied and photolithographically patterned, whereby sidewalls 32 of a channel 30 are formed. The thickness of the support layer 19 is set to be sufficient for allowing the sample to flow, specifically, for example, about 100 μm or larger in the case where the sample is blood or the like.

Subsequently, as shown in FIG. 6C, the piezoelectric substrate 12 and the lid member 20x are bonded together by heating and pressing, with the support layer 19 interposed therebetween, whereby the channel 30 is sealed.

Figure 7D:
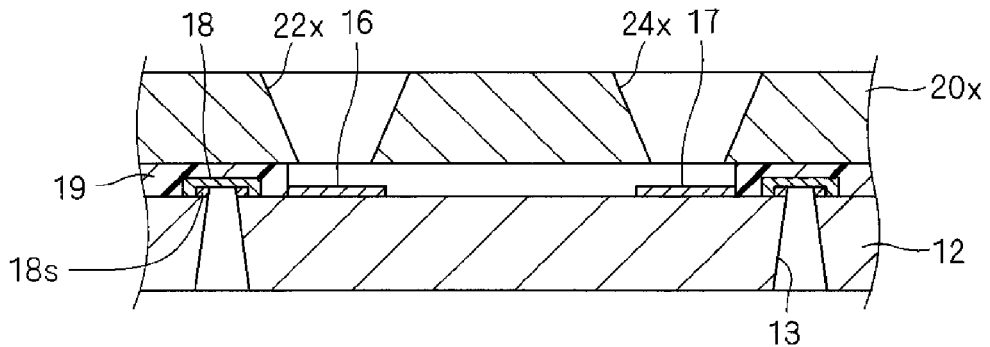

Subsequently, as shown in FIG. 7D, the vias 13 are provided in the piezoelectric substrate 12 by sandblasting, laser application, wet etching, ion milling, or the like. Considering the processing rate, sandblasting is most suitable for via-processing.

If sandblasting is performed, electrodes, functioning as etch-stop layers 18s, composed of Cu or the like are provided in advance below the respective electrode pads 18, with a thickness that is about 2% or more, for example, larger than the thickness of the piezoelectric substrate 12. For example, if the piezoelectric substrate 12 is an approximately 350 μm-thick $LiTaO_3$ substrate, the etch-stop layers 18s are formed with a thickness of about 10 μm, for example.

Figure 7E:
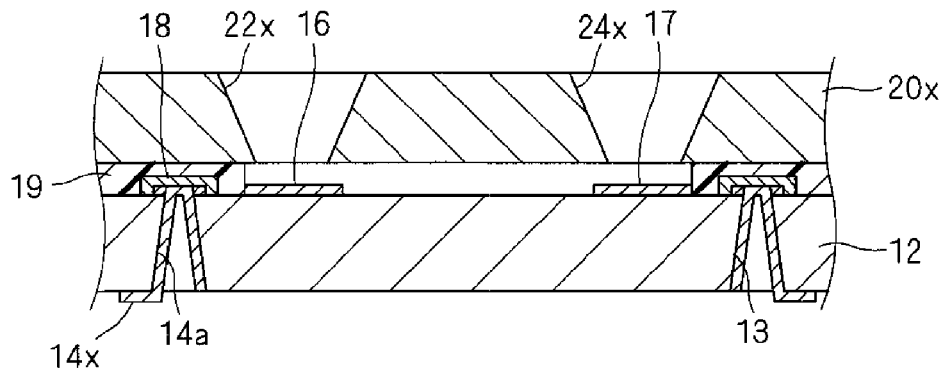

Subsequently, as shown in FIG. 7E, the in-via electrodes 14a and the extensions 14x, through which electrical signals are acquired from the top surface 12a to the bottom surface 12b of the piezoelectric substrate 12, are formed by electroplating, conductive-paste application, or the like. Considering the coating and filling characteristics of the electrodes with respect to the inner walls of the vias 13, electroplating, in particular Cu electroplating, is suitable.

Figure 7F:
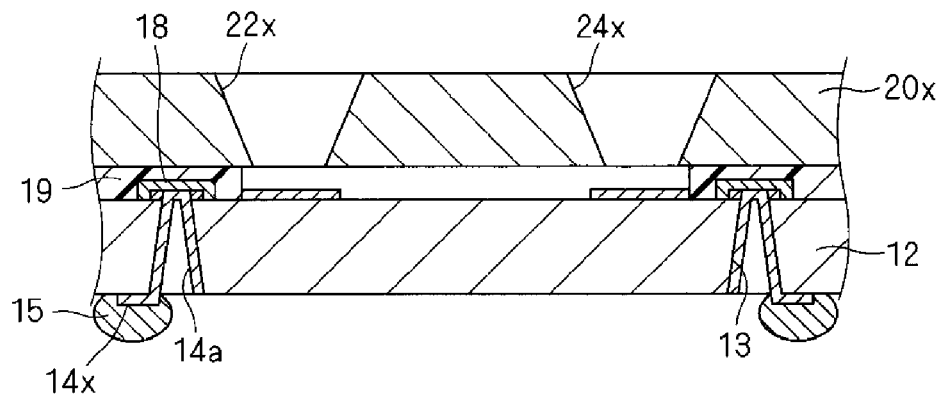

Subsequently, as shown in FIG. 7F, the solder bumps 15 are formed by solder paste printing and reflowing. In the case where the vias 13 are not filled, the solder bumps 15 are provided on the extensions 14x, i.e., beside the respective vias 13. In the case where the vias 13 are filled with electroplating, conductive paste, or the like, the solder bumps 15 can be provided directly on the vias 13, as in the first preferred embodiment.

Figure 7G:
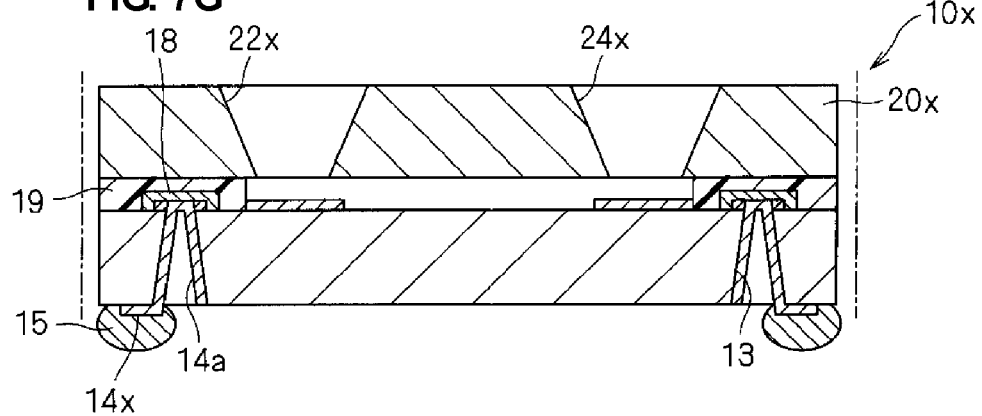

Subsequently, as shown in FIG. 7G, the parent substrate in the form of a wafer is divided into chips (child substrates) each having the in-liquid-substance detection sensor by dicing, laser application, or the like.

The bonding of the piezoelectric substrate 12 and the lid member 20x is performed while heat is applied thereto. Therefore, the difference between the coefficients of linear expansion of the two is desirably about 2 ppm/° C. or smaller, for example. Setting the difference between the coefficients of linear expansion of the piezoelectric substrate 12 and the lid member 20x to be small produces high tolerability to heat stress and causes only a small warpage of the substrates after the bonding, leading to easy processing.

In addition, the piezoelectric substrate 12 and the lid member 20x are desirably made of the same material. In such a case, there is no difference between the coefficients of linear expansion of the piezoelectric substrate 12 and the lid member 20x. This produces much higher tolerability to heat stress and causes only a much smaller warpage of the substrates after the bonding. For example, the piezoelectric substrate 12 is provided as a $LiTaO_3$ substrate, and the lid member 20x is also provided as a $LiTaO_3$ substrate.

The lid member 20x of the in-liquid-substance detection sensor 10x is a substrate, whereby a robust structure can be realized.

The in-liquid-substance detection sensors 10 and 10x described above each include the SAW devices directly provided on the surface of the channel. Therefore, compared with the case where SAW device chips are mounted on a base substrate, size reduction and detection accuracy improvement can be realized easily.

The present invention is not limited to the preferred embodiments described above, and various changes can be made thereto.

While preferred embodiments of the present invention have been described above, it is to be understood that variations and modifications will be apparent to those skilled in the art without departing the scope and spirit of the present invention. The scope of the present invention, therefore, is to be determined solely by the following claims.

What is claimed is:

1. An in-liquid-substance detection sensor comprising:
   a piezoelectric substrate;
   at least two SAW devices provided on a first major surface of the piezoelectric substrate and each having at least one IDT electrode defining a sensing portion;
   outer electrodes provided on a second major surface of the piezoelectric substrate and electrically connected to the SAW devices through vias extending through the piezoelectric substrate;
   a channel-defining member provided on the first major surface of the piezoelectric substrate so as to surround the SAW devices and a region connecting the SAW devices to each other, thereby defining sidewalls of a channel; and
   a protective member bonded to the first major surface of the piezoelectric substrate with the channel-defining member interposed therebetween, thereby sealing the channel, the protective member having at least two through holes communicating with the channel.

2. The in-liquid-substance detection sensor according to claim 1, wherein the channel-defining member is made of resin.

3. The in-liquid-substance detection sensor according to claim 1, wherein the channel-defining member is made of photosensitive resin.

4. The in-liquid-substance detection sensor according to claim 1, wherein the protective member is made of resin film.

5. The in-liquid-substance detection sensor according to claim 1, wherein the protective member is made of photosensitive resin film.

6. The in-liquid-substance detection sensor according to claim 1, wherein the protective member is made of an inorganic material.

7. The in-liquid-substance detection sensor according to claim 1, wherein a difference between coefficients of linear expansion of the protective member and the piezoelectric substrate is about 2 ppm/° C. or smaller.

8. The in-liquid-substance detection sensor according to claim 1, wherein the protective member and the piezoelectric substrate are made of the same material.

* * * * *